(12) United States Patent
Song et al.

(10) Patent No.: US 11,077,162 B2
(45) Date of Patent: Aug. 3, 2021

(54) HEART-PROTECTIVE PLANT PREPARATION FOR PREVENTING AND IMPROVING CORONARY HEART DISEASE

(71) Applicant: SHANDONG UNIVERSITY OF TECHNOLOGY, Zibo (CN)

(72) Inventors: Yuanda Song, Zibo (CN); Syed Ammar, Zibo (CN); Shaoqi Li, Zibo (CN); Wu Yang, Zibo (CN)

(73) Assignee: SHANDONG UNIVERSITY OF TECHNOLOGY, Zibo (CN)

( * ) Notice: Subject to any disclaimer, the term of this patent is extended or adjusted under 35 U.S.C. 154(b) by 0 days.

(21) Appl. No.: 17/120,162

(22) Filed: Dec. 12, 2020

(65) Prior Publication Data
US 2021/0093688 A1    Apr. 1, 2021

Related U.S. Application Data

(63) Continuation of application No. PCT/CN2019/121061, filed on Nov. 26, 2019.

(30) Foreign Application Priority Data

Dec. 11, 2018  (CN) .......................... 201811510367.2

(51) Int. Cl.
| | | |
|---|---|---|
| A61K 36/9068 | (2006.01) |
| A61K 9/00 | (2006.01) |
| A61K 9/14 | (2006.01) |
| A61K 9/48 | (2006.01) |
| A61K 36/22 | (2006.01) |
| A61K 36/287 | (2006.01) |
| A61K 36/31 | (2006.01) |
| A61K 36/45 | (2006.01) |
| A61K 36/49 | (2006.01) |
| A61K 36/52 | (2006.01) |
| A61K 36/537 | (2006.01) |
| A61K 36/54 | (2006.01) |
| A61K 36/60 | (2006.01) |
| A61K 36/63 | (2006.01) |
| A61K 36/71 | (2006.01) |
| A61K 36/738 | (2006.01) |
| A61K 36/889 | (2006.01) |
| A61K 36/8962 | (2006.01) |

(52) U.S. Cl.
CPC ........ *A61K 36/9068* (2013.01); *A61K 9/0056* (2013.01); *A61K 9/14* (2013.01); *A61K 9/48* (2013.01); *A61K 36/22* (2013.01); *A61K 36/287* (2013.01); *A61K 36/31* (2013.01); *A61K 36/45* (2013.01); *A61K 36/49* (2013.01); *A61K 36/52* (2013.01); *A61K 36/537* (2013.01); *A61K 36/54* (2013.01); *A61K 36/60* (2013.01); *A61K 36/63* (2013.01); *A61K 36/71* (2013.01); *A61K 36/738* (2013.01); *A61K 36/889* (2013.01); *A61K 36/8962* (2013.01); *A61K 2236/333* (2013.01); *A61K 2236/51* (2013.01)

(58) Field of Classification Search
CPC .... A61K 36/9068; A61K 9/0056; A61K 9/14; A61K 9/48; A61K 36/22; A61K 36/287; A61K 36/31; A61K 36/45; A61K 36/49; A61K 36/52; A61K 36/537; A61K 36/54; A61K 36/60; A61K 36/63; A61K 36/71; A61K 36/738; A61K 36/889; A61K 36/8962; A61K 2236/333; A61K 2236/51
See application file for complete search history.

(56) References Cited

U.S. PATENT DOCUMENTS

2009/0087501 A1 * 4/2009 Cummins .............. A61K 36/18
424/729

FOREIGN PATENT DOCUMENTS

| CN | 104906373 A | 9/2015 |
| CN | 105999016 A | 10/2016 |

* cited by examiner

*Primary Examiner* — Aaron J Kosar
(74) *Attorney, Agent, or Firm* — SZDC Law P.C.

(57) ABSTRACT

The present disclosure provides a natural plant preparation, including extracts of the following parts of plants: roots of *Salvia miltiorrhiza* Bunge, *Juglans regia*, *Aesculus hippocastanum* L. and *Zingiber officinale* Rosc., barks of *Cinnamomum cassia* Presl, seeds of *Sesamum indicum*, *Carica papaya* L., *Nigella damascena* L. and *Punica granatum* L., leaves of *Centaurea cyanus* L., resin of *Pistacia Lentiscus*, drupes of *Cocos nucifera* L., beans of *Theobroma cacao* L., dried pulp and kernels of *Phoenix dactylifera* L., dried pulp of *Olea europaea*, *Ficus carica* Linn., Walnut and *Vaccinium* Spp, cloves of *Allium sativum*, and petals of *Rosa* sp. The present disclosure further provides a method for preparing a plant preparation, including treating the above parts of plants with ethanol.

10 Claims, No Drawings

HEART-PROTECTIVE PLANT PREPARATION FOR PREVENTING AND IMPROVING CORONARY HEART DISEASE

CROSS-REFERENCE TO RELATED APPLICATIONS

The present application is a Continuation Application of PCT/CN2019/121061, filed on Nov. 26, 2019, which claims the priority of the Chinese patent application No. 201811510367.2, filed with the China National Intellectual Property Administration on Dec. 11, 2018 and entitled "Heart-protective plant preparation for Preventing and Improving Coronary Heart Disease", which is incorporated herein by reference in its entirety.

TECHNICAL FIELD

The present disclosure relates to a novel natural plant preparation, and particularly to a method for preventing and improving various risk factors inducing coronary heart disease or stroke.

BACKGROUND ART

Cardiovascular disease is the main cause of death in developing and developed countries. According to the report of the World Health Organization, heart disease will have become a major cause of disability and death by 2020. The most common cardiovascular disease is coronary heart disease, which kills more than 358,000 people each year and costs $108.9 billion a year. Inducements of cardiovascular disease include hypertension, anxiety, stress, smoking, high low-density lipoprotein cholesterol, diabetes, overweight/obesity, poor diet, lack of exercise, and excessive drinking. Although more and more attention has been paid to complementary and alternative medicine for cardiovascular health, there is relatively little literature on the patterns of use of complementary and alternative medicine for cardiovascular disease. Previous studies have demonstrated that by lowering blood lipid level and controlling hypertension, the onset of coronary heart disease can be minimized.

There is substantial evidence proving that hypercholesterolemia and hypertriglyceridemia can lead to atherosclerosis, coronary heart disease and stroke. High serum cholesterol, low-density lipoprotein cholesterol and relatively low high-density lipoprotein cholesterol are all important factors leading to coronary heart disease and atherosclerosis. High-concentration triglyceride, low-density low density lipoprotein cholesterol, and low-level high density lipoprotein cholesterol are known as dyslipidemia, and this process can lead to insulin resistance. Insulin resistance syndrome is characterized by comprising many inducements of cardiovascular disease, e.g., central obesity, hyperglycemia, hypertension, dyslipidemia, procoagulant factors and inflammatory markers. Studies have shown that by properly managing hypercholesterolemia, the incidence rate of coronary heart disease in diabetic patients is significantly reduced.

Acute phase reactant circulating cytokines, high-sensitivity C-reactive protein, serum albumin and fibrinogen are predictive factors of coronary heart disease onset and recurrent acute myocardial infarction. Some studies have shown that homocysteine rise is common in patients with cardiovascular disease and is highly likely to lead to heart disease. Folic acid deficiency will cause a rise in homocysteine, which is associated with an increased risk of cardiovascular disease. One of the experimental studies shows that hyperhomocysteinemia caused by folic acid depletion will increase arterial permeability and stiffness. Positional effects of elevated homocysteine level lead to oxidative damages of vascular endothelial cells, increased proliferation of smooth muscle cells, and high oxidation of atherosclerotic low density lipoprotein cholesterol. As a result, it causes endothelial dysfunction. Similarly, increased high-sensitivity C-reactive protein plays a major role in the pathogenesis of atherosclerosis. High-sensitivity C-reactive protein and other inflammation-sensitive proteins are mainly related to morphological change and rupture of plaques and acute thrombosis.

Researchers have confirmed elevated levels of circulating cytokines in patients with heart failure. The concentration of interleukin-6 is related to the severity of left ventricular dysfunction and the activation degree of sympathetic nerve and renin-angiotensin system. Thus, cytokines of interleukin-1, IL-6 and tumor necrosis factor a can cause coronary heart disease. Interleukin-6 is genetically determined, and its level determines the risk of atherosclerosis, thrombosis, and coronary heart disease.

Adiponectin is also negatively correlated with blood pressure, heart rate, total cholesterol, low density lipoprotein cholesterol and triglyceride, and is positively correlated with HDL-c. The researchers believe that high-sensitivity C-reactive protein, fibrinogen, lipoprotein and homocysteine are important biomarkers for assessing the risk of coronary heart disease, even in asymptomatic individuals with a strong family history of common risk factors for coronary heart disease.

Recently, some biomarkers are emerging for the diagnosis and treatment of heart disease such as cardiac troponin pathophysiology. (3-type natriuretic peptide is a 32-amino acid antiregulatory peptide that can cause diastole. There is a strong correlation between the value of (3-type natriuretic peptide and age and the case with acute coronary syndrome. Elevated (3-type natriuretic peptide is the cause of stroke, obstructive sleep apnea, diabetes, and left atrioventricular hypertrophy. 3CD40 is a signaling protein that will be significantly elevated in acute coronary syndrome.

Psychosocial stress also plays an important role in the occurrence of arterial hypertension, angina pectoris and myocardial infarction. Depression is an independent risk factor for the development of coronary heart disease. Therefore, stress management helps prevent adverse cardiac events. Reducing the obesity index also helps reduce the incidence rate of coronary heart disease.

Many synthetic conventional drug therapies are used in, for example, antihypertensive drugs, antiarrhythmic drugs, hypolipidemic drugs, antidiabetic drugs, and anti-obesity drugs, but their use is limited and long-term use of the drugs may adversely affect the biological system.

SUMMARY

The present disclosure provides a novel natural plant preparation that can prevent and control various coronary heart disease risk factors, including vascular inflammatory processes that cause cardiovascular events, comprising the following parts of plants extracted with 70% ethanol, i.e., roots of *Salvia miltiorrhiza* Bunge, *Juglans regia, Aesculus hippocastanum* L. and *Zingiber officinale* Rosc., bark of *Cinnamomum cassia* Presl, seeds of *Sesamum indicum, Carica papaya* L., *Nigella damascena* L. and *Punica granatum* L., leaf of *Centaurea cyanus* L., resin of *Pistacia Lentiscus*, drupe of *Cocos nucifera* L., bean of *Theobroma cacao* L., dried pulp and kernel of *Phoenix dactylifera* L., dried pulp of *Olea europaea*, *Ficus carica* Linn., Walnut and *Vaccinium* Spp, clove of *Allium sativum*, and petal of *Rosa* sp.

Optionally, the plant preparation provided by the present disclosure comprises ethanol extracts of the following parts of plants:

15-25 parts by weight, 17-23 parts by weight, or 18-22 parts by weight of roots of *Salvia miltiorrhiza* Bunge, 5-15 parts by weight, 7-13 parts by weight, or 8-12 parts by weight of roots of *Juglans regia*, 15-25 parts by weight, 17-23 parts by weight, or 18-22 parts by weight of roots of *Aesculus hippocastanum* L., 5-15 parts by weight, 7-13 parts by weight, or 8-12 parts by weight of roots of *Zingiber officinale* Rosc., 5-15 parts by weight, 7-13 parts by weight, or 8-12 parts by weight of barks of *Cinnamomum cassia* Presl, 5-15 parts by weight, 7-13 parts by weight, or 8-12 parts by weight of seeds of *Sesamum indicum*, 5-15 parts by weight, 7-13 parts by weight, or 8-12 parts by weight of seeds of *Carica papaya* L., 15-25 parts by weight, 17-23 parts by weight, or 18-22 parts by weight of seeds of *Nigella damascena* L., 5-15 parts by weight, 7-13 parts by weight, or 8-12 parts by weight of seeds of *Punica granatum* L., 15-25 parts by weight, 17-23 parts by weight, or 18-22 parts by weight of leaves of *Centaurea cyanus* L., 5-15 parts by weight, 7-13 parts by weight, or 8-12 parts by weight of resin of *Pistacia Lentiscus*, 5-15 parts by weight, 7-13 parts by weight, or 8-12 parts by weight of drupes of *Cocos nucifera* L., 5-15 parts by weight, 7-13 parts by weight, or 8-12 parts by weight of beans of *Theobroma cacao* L., 5-15 parts by weight, 7-13 parts by weight, or 8-12 parts by weight of dried pulp of *Phoenix dactylifera* L., and 5-15 parts by weight, 7-13 parts by weight, or 8-12 parts by weight of kernels of *Phoenix dactylifera* L., 5-15 parts by weight, 7-13 parts by weight, or 8-12 parts by weight of dried pulp of *Olea europaea*, 5-15 parts by weight, 7-13 parts by weight, or 8-12 parts by weight of dried pulp of *Ficus carica* Linn., 5-15 parts by weight, 7-13 parts by weight, or 8-12 parts by weight of Walnut, 5-15 parts by weight, 7-13 parts by weight, or 8-12 parts by weight of dried pulp of *Vaccinium* Spp, 5-15 parts by weight, 7-13 parts by weight, or 8-12 parts by weight of cloves of *Allium sativum*, and 5-15 parts by weight, 7-13 parts by weight, or 8-12 parts by weight of petals of *Rosa* sp.

Optionally, the plant preparation of the present disclosure comprises ethanol extracts of the following parts of plants:

20 parts by weight of roots of *Salvia miltiorrhiza* Bunge,
10 parts by weight of roots of *Juglans regia*,
20 parts by weight of roots of *Aesculus hippocastanum* L.,
10 parts by weight of roots of *Zingiber officinale* Rosc.,
10 parts by weight of barks of *Cinnamomum cassia* Presl,
10 parts by weight of seeds of *Sesamum indicum*,
10 parts by weight of seeds of *Carica papaya* L.,
20 parts by weight of seeds of *Nigella damascena* L.,
10 parts by weight of seeds of *Punica granatum* L.,
20 parts by weight of leaves of *Centaurea cyanus* L.,
10 parts by weight of resin of *Pistacia Lentiscus*,
10 parts by weight of drupes of *Cocos nucifera* L.,
10 parts by weight of beans of *Theobroma cacao* L.,
10 parts by weight of dried pulp of *Phoenix dactylifera* L., and 10 parts by weight of kernels of *Phoenix dactylifera* L.,
10 parts by weight of dried pulp of *Olea europaea*,
10 parts by weight of dried pulp of *Ficus carica* Linn.,
10 parts by weight of Walnut,
10 parts by weight of dried pulp of *Vaccinium* Spp,
10 parts by weight of cloves of *Allium sativum*, and
10 parts by weight of petals of *Rosa* sp.

Optionally, the above-described natural plant preparation is formulated into powder, capsules, tablets, granules, pills, lozenges, etc.

Optionally, the various coronary heart disease risk factors are selected from one or more of: dyslipidemia, obesity, hypertension, glucose intolerance, hyperhomocysteinemia, vascular inflammation, and anxiety and stress.

The present disclosure further provides a novel method for preparing a plant preparation, comprising the steps of: treating the above-described plant parts (Table 1) with 70% ethanol at 70-80° C., and maintaining the pH of the solution at 7-10. Active compounds are separated using thin layer chromatography and high performance liquid chromatography, and the molecular characterization of the plant extracts is detected using infrared spectroscopy and nuclear magnetic resonance.

The present disclosure further provides use of the above-described plant preparation in the preparation of a medicament for the prevention and control the risk factors of coronary heart disease and stroke.

The present disclosure further provides use of the above-described plant preparation in the preparation of a medicament for the prevention and control the risk factors of coronary heart disease and stroke.

The present disclosure further provides a method for preventing and controlling the risk factors of coronary heart disease and stroke, comprising administering a therapeutically effective amount of the plant preparation according to any one of claims 1-5 to a subject in need thereof.

DETAILED DESCRIPTION OF EMBODIMENTS

The present disclosure relates to a novel plant preparation and a method of treating and controlling various inducements that induce coronary heart disease or stroke using the novel plant preparation. The preparation of the present disclosure is used for the treatment and control of dyslipidemia, obesity, hypertension, glucose intolerance, hyperhomocysteinemia, vascular inflammation, and anxiety and stress.

EXAMPLES

TABLE 1

1. Extraction and detection of active substances

| Serial number | Scinific name | Tissue sites | Addition amount of tissues, parts by weight |
| --- | --- | --- | --- |
| 1 | Salvia miltiorrhiza Bunge | root | 20 |
| 2 | Centaurea cyanus L. | leaf | 20 |
| 3 | Cinnamomum cassia Presl | bark | 10 |
| 4 | Juglans regia | root | 10 |
| 5 | Aesculus hippocastanum L. | root | 20 |
| 6 | Sesamum indicum | seed | 10 |
| 7 | Pistacia Lentiscus | resin | 10 |
| 8 | Cocos nucifera L. | drupe | 10 |
| 9 | Carica papaya L. | seed | 10 |
| 10 | Nigella damascena L. | seed | 20 |
| 11 | Phoenix dactylifera L. | dried pulp and kernel | 10 for each |
| 12 | Walnut | dried nut | 10 |

TABLE 1-continued

1. Extraction and detection of active substances

| Serial number | Scinific name | Tissue sites | Addition amount of tissues, parts by weight |
|---|---|---|---|
| 13 | Theobroma cacao L. | bean | 10 |
| 14 | Olea europaea | dried pulp | 10 |
| 15 | Ficus carica Linn. | dried pulp | 10 |
| 16 | Vaccinium Spp | dried pulp | 10 |
| 17 | Punica granatum L. | seed | 10 |
| 18 | Allium sativum | clove | 10 |
| 19 | Zingiber officinale Rosc. | root | 10 |
| 20 | Rosa Damascena | petal | 10 |

Various samples were prepared according to the tissue site and addition amount of tissues of each plant in Table 1. The samples were thoroughly washed with deionized water to remove any contaminants, and the above samples were mixed uniformly and then ground with the aid of liquid nitrogen to prepare crude powders, which were then extracted with ethanol, methanol, acetone and water separately. The selection of solvents was based on their polarity, in a descending order of polarity (i.e. water>methanol>ethanol>acetone), as different types of bioactive compounds have different affinities to solvents of different polarities.

For extraction, equal parts of crude powders (5 g) were accurately weighed into four 250 mL flasks and shaken overnight (16-20 h) with 50 ml of ethanol, methanol, acetone and water, respectively, at a ratio of 1:10. At indoor temperature, and after shaking overnight, all the samples were centrifuged at 4000 rpm for 10 minutes and then the supernatant was vacuum filtered through qualitative filter paper. The residues were then resuspended in another 50 ml of ethanol, methanol, acetone and water, respectively. The process was repeated twice. The combined filtrate was transferred to a pre-weighed glass plate, which was placed in a 40° C. hot air oven for 4 hours to evaporate the organic solvents, and then the filtrate was freeze-dried using freeze drying equipment. After freeze drying, the dry weight of the samples was recorded and the samples were stored at −80° C. for further use.

The four extracts were analyzed and detected by LC-ESI-MS separately, and the detection results showed that the descending order of active substance was ethanol>methanol>acetone>water. The ethanol extract was thus selected and formulated into capsules (500 mg/capsule) for the next experiment.

2. Subjects

A total of 112 eligible subjects with cardiovascular disease were randomly divided into two groups: PHF treatment group (n=78) and placebo group (n=34) -administered orally at 500 mg (one capsule) once a day for 12 weeks.

3. Inclusion Criteria

The inclusion criteria were being 35-72 years old, being obese (BMI×30 kg m$^{-2}$) and being diagnosed as suffering from one of the cardiovascular inducements, i.e., type 2 diabetes, ischemic heart disease, hypertension, hypercholesterolemia or vascular inflammation.

4. Exclusion Criteria

Exclusion criteria were diagnosis of life-threatening complications, including thyroid diseases; being within 6 weeks after coronary artery bypass grafting; being within 1 month after the occurrence of myocardial infarction; being within 6 months after angioplasty; left main coronary artery stenosis>50%; unresponsive congestive heart failure; malignant uncontrolled arrhythmia; homozygous hypercholesterolemia; severe mental illness; current alcohol or drug abuse; current smoking; current pregnant or lactating women, previous bariatric surgery, other diseases that directly affect body weight (e.g. lead toxicity, malignant tumors).

5. Results

TABLE 2

| Detection items | Herbal medicine treatment group (n = 78) | 12 weeks later | placebo group (n = 34) | 12 weeks later |
|---|---|---|---|---|
| low density lipoprotein cholesterol (mg/dL) | 134.2 ± 25.4 | 102.2 ± 31.6 | 138.4 ± 24.5 | 134.2 ± 30.1 |
| high density lipoprotein cholesterol (mg/dL) | 44.4 ± 13.4 | 50.20 ± 10.1 | 44.3 ± 11.6 | 39.4 ± 13.1 |
| triglyceride (mg/dL) | 202.6 ± 64 | 162.12 ± 44 | 188.7 ± 18.10 | 215 ± 39 |
| total cholesterol (mg/dL) | 212.8 ± 18.5 | 180.1 ± 22.3 | 210.6 ± 31.1 | 209.8 ± 32.4 |
| interleukin-6 | 14.7 ± 11.19 | 4.2 ± 5.86 | 13.7 ± 12.18 | 12.9 ± 11.43 |
| interleukin | 5.1 ± 3.56 | 2.04 ± 4.93 | 4.8 ± 3.56 | 4.5 ± 2.33 |
| tumor necrosis factor | 26.7 ± 9.51 | 11.2 ± 7.31 | 25.7 ± 10.62 | 25.81 ± 8.11 |
| body mass index (kg/m$^2$) | 31.2 ± 3.2 | 26.2 ± 1.8 | 30.6 ± 4.1 | 28.76 ± 2.5 |
| body weight (kg) | 88.4 ± 15.2 | 82.4 ± 21.1 | 84.8 ± 12.8 | 82.7 ± 10.2 |
| fasting blood glucose (mg/dL) | 185.2 ± 35.2 | 161.3 ± 31 | 190.2 ± 44.2 | 188.7 ± 1 |
| glycosylated hemoglobin (%) | 7.9 ± 1.2 | 6.1 ± 1.4 | 8.2 ± 1.3 | 7.9 ± 1.1 |

INDUSTRIAL APPLICABILITY

The present disclosure relates to a novel plant preparation and a method of treating and controlling various inducements that induce coronary heart disease or stroke using the novel plant preparation. The preparation of the present disclosure is used for the treatment and control of dyslipidemia, obesity, hypertension, glucose intolerance, hyperhomocysteinemia, vascular inflammation, and anxiety and stress.

The invention claimed is:

1. A plant preparation, comprising in an oral dosage form therapeutically effective amounts of ethanol extracts of following parts of plants:

roots of *Salvia miltiorrhiza* Bunge, *Juglans regia, Aesculus hippocastanum* L. and *Zingiber officinale* Rosc., barks of *Cinnamomum cassia* Presl, seeds of *Sesamum indicum, Carica papaya* L., *Nigella damascena* L. and *Punica granatum* L., leaves of *Centaurea cyanus* L., resin of *Pistacia Lentiscus*, drupes of *Cocos nucifera* L., beans of *Theobroma cacao* L., dried pulp and kernels of *Phoenix dactylifera* L., dried pulp of *Olea europaea, Ficus carica* Linn., walnut, and *Vaccinium* Spp, cloves of *Allium sativum*, and petals of *Rosa* sp.

2. The plant preparation according to claim 1, comprising:
- 15-25 parts by weight of roots of *Salvia miltiorrhiza* Bunge,
- 5-15 parts by weight of roots of *Juglans regia*,
- 15-25 parts by weight of roots of *Aesculus hippocastanum* L.,
- 5-15 parts by weight of roots of *Zingiber officinale* Rosc.,
- 5-15 parts by weight of barks of *Cinnamomum cassia* Presl,
- 5-15 parts by weight of seeds of *Sesamum indicum*,
- 5-15 parts by weight of seeds of *Carica papaya* L.,
- 15-25 parts by weight of seeds of *Nigella damascena* L.,
- 5-15 parts by weight of seeds of *Punica granatum* L.,
- 15-25 parts by weight of leaves of *Centaurea cyanus* L.,
- 5-15 parts by weight of resin of *Pistacia Lentiscus*,
- 5-15 parts by weight of drupes of *Cocos nucifera* L.,
- 5-15 parts by weight of beans of *Theobroma cacao* L.,
- 5-15 parts by weight of dried pulp of *Phoenix dactylifera* L.,
- 5-15 parts by weight of kernels of *Phoenix dactylifera* L.,
- 5-15 parts by weight of dried pulp of *Olea europaea*,
- 5-15 parts by weight of dried pulp of *Ficus carica* Linn.,
- 5-15 parts by weight of walnut,
- 5-15 parts by weight of dried pulp of *Vaccinium* spp,
- 5-15 parts by weight of cloves of *Allium sativum*, and
- 5-15 parts by weight of petals of *Rosa* sp.

3. The plant preparation according to claim 2, comprising the ethanol extracts of the following parts of plants:
- 20 parts by weight of roots of *Salvia miltiorrhiza* Bunge,
- 10 parts by weight of roots of *Juglans regia*,
- 20 parts by weight of roots of *Aesculus hippocastanum* L.,
- 10 parts by weight of roots of *Zingiber officinale* Rosc.,
- 10 parts by weight of barks of *Cinnamomum cassia* Presl,
- 10 parts by weight of seeds of *Sesamum indicum*,
- 10 parts by weight of seeds of *Carica papaya* L.,
- 20 parts by weight of seeds of *Nigella damascena* L.,
- 10 parts by weight of seeds of *Punica granatum* L.,
- 20 parts by weight of leaves of *Centaurea cyanus* L.,
- 10 parts by weight of resin of *Pistacia Lentiscus*,
- 10 parts by weight of drupes of *Cocos nucifera* L.,
- 10 parts by weight of beans of *Theobroma cacao* L.,
- 10 parts by weight of dried pulp of *Phoenix dactylifera* L.,
- 10 parts by weight of kernels of *Phoenix dactylifera* L.,
- 10 parts by weight of dried pulp of *Olea europaea*,
- 10 parts by weight of dried pulp of *Ficus carica* Linn.,
- 10 parts by weight of walnut,
- 10 parts by weight of dried pulp of *Vaccinium* Spp,
- 10 parts by weight of cloves of *Allium sativum*, and
- 10 parts by weight of petals of *Rosa* sp.

4. The plant preparation according to claim 1, wherein the plant preparation is formulated into a dosage form selected from the group consisting of powders, capsules, tablets, granules, pills, and lozenges.

5. A method for preparing a plant preparation according to claim 1, the method comprising the steps of:
- providing parts of plants comprising roots of *Salvia miltiorrhiza* Bunge, *Juglans regia*, *Aesculus hippocastanum* L. and *Zingiber officinale* Rosc., barks of *Cinnamomum cassia* Presl, seeds of *Sesamum indicum*, *Carica papaya* L., *Nigella damascena* L. and *Punica granatum* L., leaves of *Centaurea cyanus* L., resin of *Pistacia Lentiscus*, drupes of *Cocos nucifera* L., beans of *Theobroma cacao* L., dried pulp and kernels of *Phoenix dactylifera* L., dried pulp of *Olea europaea*, *Ficus carica* Linn., walnut, and *Vaccinium* Spp, cloves of *Allium sativum*, and petals of *Rosa* sp.
- treating the parts of the plants, at 70-80° C., with ethanol, and
- maintaining pH of the resulting solution between pH 7 and pH 10.

6. The method according to claim 5, wherein the ethanol is 60-80 vol % ethanol or 70 vol % ethanol.

7. The method according to claim 5, wherein the provided parts of plants are in powder form.

8. The method according to claim 5, wherein the duration for treating the parts of plants with ethanol is 16-20 h.

9. The method according to claim 5, further comprising a drying step to remove the organic solvents and/or provide the plant preparation as a dried plant preparation.

10. The method according to claim 5, wherein the drying step comprises drying by a hot air oven to evaporate organic solvents followed by freeze drying.

* * * * *

UNITED STATES PATENT AND TRADEMARK OFFICE
CERTIFICATE OF CORRECTION

PATENT NO. : 11,077,162 B2
APPLICATION NO. : 17/120162
DATED : August 3, 2021
INVENTOR(S) : Yuanda Song et al.

Page 1 of 1

It is certified that error appears in the above-identified patent and that said Letters Patent is hereby corrected as shown below:

On the Title Page

(54) in the title, changed from:
"IMPROVING"
To:
"CONTROLLING"

(72) 2nd Inventor, changed from:
"Syed Ammar, Zibo (CN)"
To:
"Syed Ammar Hussain, Zibo (CN)"

In the Specification

Column 1, Line 3, changed from:
"IMPROVING"
To:
"CONTROLLING"

Column 1, Lines 13-14, changed from:
"Improving"
To:
"Controlling"

Column 1, Line 21, changed from:
"improving"
To:
"controlling"

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*